US012586667B2

(12) United States Patent
Kaftan et al.

(10) Patent No.: US 12,586,667 B2
(45) Date of Patent: Mar. 24, 2026

(54) PSEUDONYMIZED STORAGE AND RETRIEVAL OF MEDICAL DATA AND INFORMATION

(71) Applicant: Siemens Healthineers AG, Forchheim (DE)

(72) Inventors: Jens Kaftan, Bamberg (DE); Jonathan Sperl, Bamberg (DE); Nagineni Muralidhar Chowdary, Bangalore (IN); Kishan Venkatesan, Bangalore (IN); Mario Amrehn, Fuerth (DE); Sven Bauer, Herzogenaurach (DE)

(73) Assignee: Siemens Healthineers AG, Forchheim (DE)

( * ) Notice: Subject to any disclaimer, the term of this patent is extended or adjusted under 35 U.S.C. 154(b) by 286 days.

(21) Appl. No.: 17/873,535

(22) Filed: Jul. 26, 2022

(65) Prior Publication Data

US 2023/0033417 A1     Feb. 2, 2023

(30) Foreign Application Priority Data

Jul. 29, 2021     (EP) ..................................... 21188546

(51) Int. Cl.
*G16H 10/60*          (2018.01)
*G06F 21/62*          (2013.01)
*H04L 9/40*           (2022.01)

(52) U.S. Cl.
CPC ......... *G16H 10/60* (2018.01); *G06F 21/6254* (2013.01); *H04L 63/0407* (2013.01); *H04L 2209/42* (2013.01)

(58) Field of Classification Search
CPC . G16H 10/60; G06F 21/6254; H04L 63/0407; H04L 2209/42
See application file for complete search history.

(56) References Cited

U.S. PATENT DOCUMENTS

| | | | | |
|---|---|---|---|---|
| 10,230,703 | B1 * | 3/2019 | Lepore .................. | H04L 9/0894 |
| 10,699,410 | B2 | 6/2020 | Pheiffer et al. | |
| 11,737,668 | B2 * | 8/2023 | Shelton, IV .......... | A61B 90/37 |
| | | | | 709/233 |
| 2005/0043964 | A1 * | 2/2005 | Thielscher ............. | G06Q 10/10 |
| | | | | 705/50 |
| 2013/0138948 | A1 * | 5/2013 | Solotorevsky ...... | H04L 12/1403 |
| | | | | 713/153 |

(Continued)

FOREIGN PATENT DOCUMENTS

| | | | | |
|---|---|---|---|---|
| EP | 1603070 | A2 * | 12/2005 | .......... G06F 19/321 |
| EP | 3828816 | A1 | 6/2021 | |

OTHER PUBLICATIONS

Neubauer et al., "A methodology for the pseudonymization of medical data," international journal of medical informatics 80 (2011) 190-204; doi:10.1016/j.ijmedinf.2010.10.016. (Year: 2011).*

(Continued)

*Primary Examiner* — Jonathon A. Szumny
(74) *Attorney, Agent, or Firm* — Harness, Dickey & Pierce, P.L.C.

(57) ABSTRACT

Techniques of storing and retrieving medical data and information are provided. Medical result information can be stored on a long-term data repository in a shared network, e.g., the Internet. Pseudonymized identifiers of patients can be used to retrieve such data and information.

24 Claims, 4 Drawing Sheets

(56) References Cited

U.S. PATENT DOCUMENTS

| | | | | |
|---|---|---|---|---|
| 2013/0239226 A1* | 9/2013 | Miyakawa | ........... | G06Q 10/103 726/26 |
| 2014/0136237 A1* | 5/2014 | Anderson | ............. | G16H 10/60 705/3 |
| 2014/0214683 A1* | 7/2014 | Dominick | ............. | G16H 30/20 705/51 |
| 2014/0236628 A1 | 8/2014 | Friese et al. | | |
| 2014/0298030 A1* | 10/2014 | Akiyama | ............. | H04L 63/062 713/172 |
| 2016/0147945 A1* | 5/2016 | MacCarthy | ........... | H04W 12/02 705/51 |
| 2016/0342812 A1* | 11/2016 | Lynch | ................. | H04L 63/0421 |
| 2017/0091388 A1* | 3/2017 | Zolla | ...................... | G16H 10/60 |
| 2017/0372096 A1* | 12/2017 | Yousfi | ................. | G06F 21/6254 |
| 2018/0013547 A1* | 1/2018 | Giura | .................. | H04L 63/1408 |
| 2018/0276248 A1* | 9/2018 | Burkett | .................. | G16H 30/20 |
| 2019/0122753 A1* | 4/2019 | Friese | ..................... | G16Z 99/00 |
| 2019/0205566 A1* | 7/2019 | Shelton, IV | ........ | G06F 21/6254 |
| 2020/0118317 A1* | 4/2020 | Mysore Siddu | .......... | G06T 7/73 |
| 2020/0334817 A1 | 10/2020 | Irving et al. | | |
| 2020/0388363 A1* | 12/2020 | Docktor | ................. | G16H 10/60 |
| 2021/0049301 A1* | 2/2021 | Gregori | .............. | H04L 63/0442 |
| 2021/0158910 A1* | 5/2021 | Galassi | .................. | G16H 10/60 |
| 2021/0166406 A1 | 6/2021 | Sperl et al. | | |
| 2021/0166807 A1* | 6/2021 | Quennesson | .......... | G06N 20/00 |
| 2022/0101966 A1* | 3/2022 | Goldstein | ............. | G16H 10/60 |
| 2022/0375087 A1* | 11/2022 | Ironside | ................ | G16H 30/40 |
| 2022/0383499 A1 | 12/2022 | Sperl et al. | | |

OTHER PUBLICATIONS

Abouakil et al., "Data Models for the Pseudonymization of DICOM Data," Proceedings of the 44th Hawaii International Conference on System Sciences—2011. (Year: 2011).*

Noumeir et al., "Pseudonymization of Radiology Data for Research Purposes," Journal of Digital Imaging, vol. 20, No. 3 Sep. 2007: pp. 284-295. (Year: 2007).*

Tiina, Rajala et al: "Development of a Research Dedicated Archival System (TARAS) in a University Hospital"; Journal of Digital Imaging; the Journal of the Society for Computer Applications in Radiology; Springer-Verlag; NE, vol. 24, No. 5; Nov. 2, 2010 (Nov. 2, 2010), pp. 864-873; XP019957045; ISSN: 1618-727X; DOI:10. 1007/S10278-010-9350-1.

Silva, Jorge Miguel et al: "Controlled searching in reversibly de-identified medical imaging archives"; Journal of Biomedical Informatics; Academic Press; New York; NY, US; vol. 77, Dec. 7, 2017; pp. 81-90; XP085337355; ISSN: 1532-0464; DOI: 10.1016/ J.JBI.2017.12.002.

* cited by examiner

PSEUDONYMIZED STORAGE AND RETRIEVAL OF MEDICAL DATA AND INFORMATION

CROSS-REFERENCE TO RELATED APPLICATION(S)

The present application claims priority under 35 U.S.C. § 119 to European Patent Application No. EP 21188546.2, filed Jul. 29, 2021, the entire contents of which are incorporated herein by reference.

FIELD

Various examples of the disclosure relate to processing medical data of a patient to perform an analysis of diseases. Various examples of the disclosure specifically relate to retrieving prior medical result information of the patient from a long-term data repository based on at least one pseudonymized identifier determined based on plain information of the patient and processing medical data of the patient obtained later based on the prior medical result information.

BACKGROUND

Recently, artificial-intelligence-based (AI-based) systems, including machine-learning-based computer-aided diagnosis (CAD) systems have become available for assisting radiologists in assessing medical data (e.g., medical imaging data) from various modalities, e.g., computed tomography, CT, magnetic resonance imaging, MRI, mammography, X-ray fluoroscopy, electroencephalography, EEG, Electrocardiograph, ECG, etc., and from various regions of the human body (e.g., chest, head, abdomen, etc.).

For assessments of certain diseases, and/or for monitoring the progress/time-dependency of certain diseases (longitudinal analysis), it is sometimes helpful to compare two or more medical data of the same patient from different points in time. For example, this can be used for determining the growth rate of a nodule or for determining a change in the structure of the spine of a patient.

It can be, in particular, desirable to perform a longitudinal analysis in a cloud-based system. A cloud-based system can denote a system of one or more servers which is located off-premise of a hospital, e.g., outside the local network of the hospital where a patient is treated.

SUMMARY

There are certain problems that complicate the handling of such multi-time point situations in a cloud-based system. Due to data privacy reasons, it is often not allowed to persistently store medical data of a patient outside of the hospital IT equipment, at least not together with personal health information (PHI) or information identifying the patient. Further, transferring additional medical data to or from the data repository outside the hospital to the local hospital storage, such as a picture archiving and communication system (PACS), takes a large amount of time and occupies significant storage space of the data repository due to the large file size of medical data. Additionally, the local hospital storage may not be reachable from outside of the hospital for querying/retrieving data due to security considerations and thereby it is not possible to obtain medical data removed PHI from outside of the hospital.

Accordingly, there is a need for advanced techniques that mitigate or overcome the above-identified drawbacks or restrictions. There is a need for advanced techniques of processing medical data to perform a longitudinal analysis of diseases.

This need is met by example embodiments.

A computer-implemented method is provided. The computer-implemented method includes obtaining medical data. The medical data includes medical imaging data that is captured for an anatomical region of the patient. The medical data also includes non-pseudonymized information of the patient. The computer-implemented method also includes determining at least one pseudonymized identifier that is associated with the patient based on the non-pseudonymized information of the patient. Further, the computer-implemented method includes retrieving prior medical result information from a long-term data repository based on the at least one pseudonymized identifier. The method also includes processing the medical data based on the prior medical result information.

A computer program or a computer-program product or a computer-readable storage medium including program code is provided. The program code can be loaded and executed by at least one processor. Upon loading and executing the program code, the at least one processor performs a computer-implemented method. The computer-implemented method includes obtaining medical data. The medical data includes medical imaging data that is captured for an anatomical region of the patient. The medical data also includes non-pseudonymized information of the patient. The computer-implemented method also includes determining at least one pseudonymized identifier that is associated with the patient based on the non-pseudonymized information of the patient. Further, the computer-implemented method includes retrieving prior medical result information from a long-term data repository based on the at least one pseudonymized identifier. The method also includes processing the medical data based on the prior medical result information.

A device including a computing unit is provided. The computing unit is configured to cause the device to obtain medical data. The medical data includes medical imaging data that is captured for an anatomical region of the patient. The medical data also includes non-pseudonymized information of the patient. The computing unit is also configured to cause the device to determine at least one pseudonymized identifier that is associated with the patient based on the non-pseudonymized information of the patient. Further, the computing unit is also configured to cause the device retrieve prior medical result information from a long-term data repository based on the at least one pseudonymized identifier. The computing unit is also configured to cause the device to process the medical data based on the prior medical result information.

It is to be understood that the features mentioned above and those yet to be explained below may be used not only in the respective combinations indicated, but also in other combinations or in isolation without departing from the scope of the invention.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of this disclosure.

FIG. 3 is a flowchart of a method according to various examples.

FIG. 5 a block diagram of a device according to various examples.

DETAILED DESCRIPTION

Figure 1:
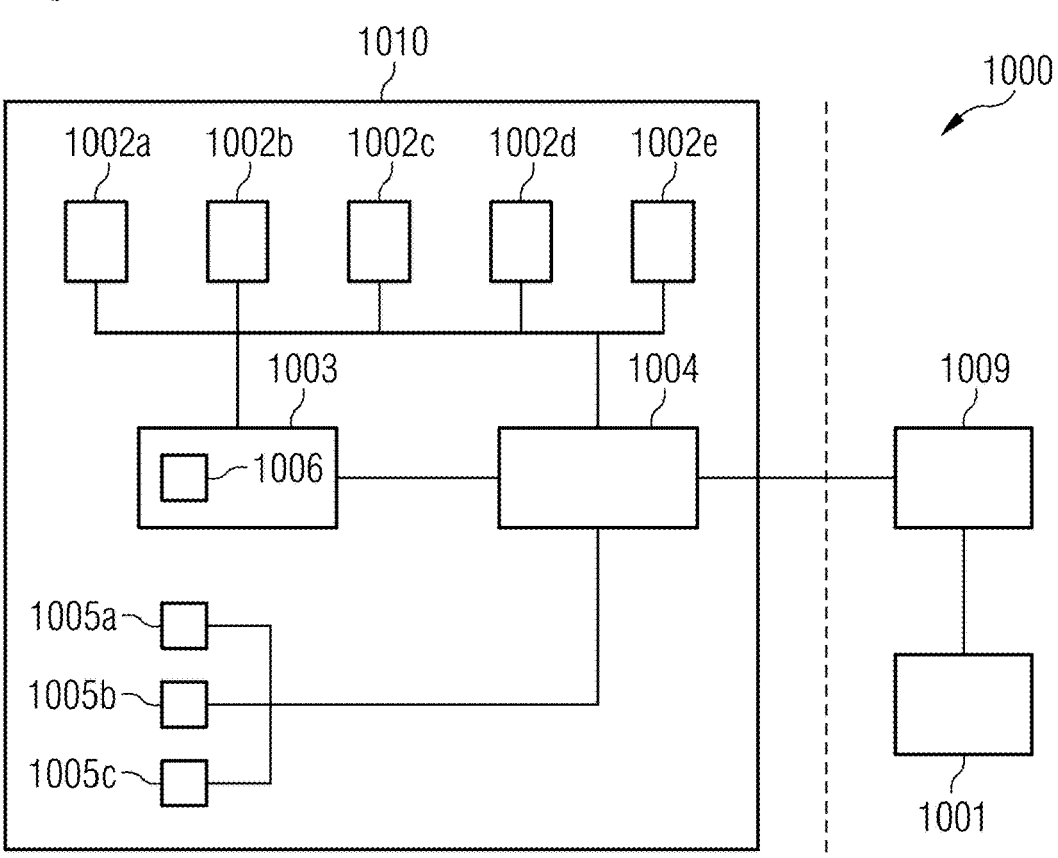
FIG. 1 schematically illustrates details with respect to a system according to various examples.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired.

It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation (s) disclosed herein. In addition, anyone or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various techniques disclosed herein generally relate to processing medical data of a patient to perform or facilitate a longitudinal analysis of diseases.

According to the disclosure, the medical data may comprise medical imaging data captured for an anatomical region of the patient. The medical data may alternatively or additionally comprise data of biochemical tests, e.g., blood tests, urine tests, and etc. The medical data may also comprise EEG and ECG data. The medical imaging data may be 1-D data obtained directly from a corresponding scanner, 2-D reconstructed images, or 3-D reconstructed slices comprising multiple voxels. The medical imaging data may comprise at least one of MRI image data, X-ray image data, CT image data, ultrasound image data, or any other kind of medical image data. Such medical imaging data can be processed to derive medical result information.

The medical data to be processed can be obtained in various ways. According to the disclosure, the medical data may be obtained from at least one of the following medical equipment: a medical imaging scanner (e.g., MRI, CT, X-ray, positron emission tomography (PET), single-photon emission computed tomography (SCPET)), a hematology analyzer, an EEG, an ECG and etc. Respective medical equipment may be controlled to acquire the medical data or at least parts thereof. Additionally or alternatively, the medical data may be obtained from a PACS within a hospital local network.

The medical data may further include plain information (also referred to as first information or non-pseudonymized information) of the patient. For example, the plain information of the patient may comprise at least one of an identity number, an issuer of the identity number, a name, date of birth, a gender, and an original unique identity number. Such information may be available in clear format, i.e., not pseudonymized or encrypted.

As a general rule, according to the disclosure, various information elements may be taken into account when performing the longitudinal analysis. For instance, it would be possible to take into account medical data obtained at an earlier point in time. Alternatively or additionally, it would be possible to take into account auxiliary data. The auxiliary data may, e.g., pertain to a context of medical imaging. The auxiliary data may pertain to patient-specific information. Alternatively or additionally, the longitudinal analysis of diseases of the patient can be performed or facilitated by processing the medical data of the patient based on prior medical result information of the patient.

According to the disclosure, the prior medical result information of the patient may comprise medical result information obtained at one or multiple prior time points. Thus, the prior medical result information may provide information regarding a health state of the patient at an earlier point in time.

According to the disclosure, each of the prior medical result information of the patient may comprise at least one of the following elements: information on the anatomy of the patient, a size of a lesion or a tumor, a segmentation of the nodule or the tumor, a position of the nodule or the tumor, a stage of the tumor, a growth rate of the nodule or the tumor, a quantification of physiological property, such as a value of blood pressure, a value of heart rate, a glycemic index, a height, and a weight.

Each of the prior medical result information of the patient may alternatively or optionally comprise a diagnostic result or findings by a doctor or a physician, such as properties of function of an organ or a part of human body (e.g., a nervous system or a central nervous system). Other elements comprised in each of the prior medical result information may include prescription data associated with each of the prior medical result information and/or original medical imaging data obtained for diagnosis.

Thus, generally, medical result information may be derived from medical data. The medical result information may be obtained by processing respective medical data and, specifically, the medical imaging data. The medical result information may specify one or more hidden values included in the medical data.

The prior medical result information may further comprise or be associated with at least one pseudonymized identifier associated with the patient. The pseudonymized identifier can help to match the prior medical result information to a given patient, while maintaining privacy.

The prior medical result information may be stored in a long-term data repository outside a hospital (i.e., not in a local area network of the hospital). This storage may be organized based on the pseudonymized identifier. The storage can thus be a cloud-based storage. According to the disclosure, the prior medical result information may be stored at a long-term data repository. The long-term data repository may be located in a shared network outside of a hospital local network, e.g., in the Internet. The prior medical result information may thus be generally accessible from different hospitals and different users.

According to the disclosure, at least one pseudonymized identifier associated with the patient is determined based on plain information of the patient included in the medical data.

Such determination of the at least one pseudonymized identifier may be implemented at a device inside a hospital local network or at a cloud server in a shared network.

Then, the prior medical result information is retrieved from a long-term data repository based on the pseudonymized patient identifier. The medical data can then be processed based on the prior medical result information.

According to the disclosure, the at least one pseudonymized identifier may comprise at least one of a pseudonymized identity number, a pseudonymized issuer of the identity number, a pseudonymized name, a pseudonymized date of birth, a pseudonymized gender, and a pseudonymized original unique identity number. These are only example information elements. The at least one pseudonymized identifier may include other information elements or additional information elements.

According to the disclosure, the at least one pseudonymized identifier can thus hide plain information associated with the patient. The pseudonymized identifier can maintain privacy.

The at least one pseudonymized identifier associated with the patient may be determined based on the plain information of the patient and may have a one-to-one, one-to-many, many-to-one, or many-to-many mapping with the plain information of the patient.

Depending on the type of mapping, parsing of the at least one pseudonymized identifier—i.e., reconstruction of plain information based on the at least one pseudonymized identifier—may or may not yield ambiguities.

For instance, the pseudonymized identity number may be determined based on only the identity number of the patient, or on both the identity number and the name of the patient. Additionally or alternatively, both the pseudonymized identity number and the pseudonymized name may be determined based on both the identity number and the name of the patient.

As a general rule, one-to-one, one-to-many, many-to-one, or many-to-many mappings from plain patient information to at least one pseudonymized identifier may comprise a function or a lookup table; i.e., the at least one pseudonymized identifier may be determined based on the plain information using the function or the lookup table. For example, such mappings may be based on a hash function/ algorithm, on a salted secure hash function/algorithm, or on a codebook, such as, American Standard Code for Information Interchange (US-ASCII), Unicode (or Universal Coded Character Set) Transformation Format—8-bit (UTF-8), UTF-16, UTF-32.

According to the disclosure, the function or the lookup table may be stored in at least one computing device within the hospital and after obtaining the prior medical result information/medical data from the long-term data repository, the at least one computing device may executing a reverse transformation associated with the function or the lookup table to derive plain information of the patient from the at least one pseudonymized identifier.

According to the disclosure, the function or the lookup table may be stored in a cloud server or even the long-term data repository of the shared network and after obtaining the prior medical result information/medical data from the long-term data repository, the cloud server may executing a reverse transformation associated with the function or the lookup table to derive plain information of the patient from the at least one pseudonymized identifier.

The pseudonymized identifier can be stored in the long-term data repository.

According to the disclosure, if certain attributes of the plain information, such as name, cannot be stored along with the medical result information in the long-term data repository, instead of such attributes a hash value thereof can be stored and compared.

Additionally or optionally, in order to avoid that PHI data for a certain patient from an institution, e.g., a hospital or a medical school, can be reconstructed in the long-term data repository (e.g. because the same patient name or the same date of birth being mapped to the same hash value), a salted hash value can be used, wherein the salt differs from institution to institution. The key-hashed version of the PHI information (e.g., name, data of birth), i.e., the at least one pseudonymized identifier, in one realization is being added to the DICOM header before the data leaves the hospital's premises and the corresponding key is private to the hospital institution without the need of the patient matching algorithm to have knowledge about this key.

By using the at least one pseudonymized identifier associated with the patient to identify the prior medical result information and/or the medical data, data privacy can be ensured while retrieving prior medical result information and/or medical data of a specific patient can be facilitated. Further, storage burdens on local hospital storage, such as the PACS, can be significantly relieved by just temporarily storing medical data and/or medical result information of patients in the local hospital storage. Additionally, if only medical result information of patients is stored in the long-term data repository (rather than the medical data itself, which typically includes medical imaging data and is, thus oftentimes significantly larger than the processed medical result information), time for transferring data of patients to or from the long-term data repository is reduced and storage spaces for storing the data of patients also reduced.

In addition to the medical result information, it would be possible that also the medical data, e.g., medical images, etc., are stored in the long-term data repository, e.g., in a pseudonymized manner.

If the medical data are also stored in the long-term data repository in a pseudonymized way, such medical data can be queried/retrieved from outside of a hospital and thereby facilitate education and research usages.

As a general rule, medical data and/or the pseudonymized identifiers and/or medical result information may be encoded according to communication protocol standards, such as the Digital Imaging and Communications in Medicine (DICOM) standard.

According to various examples, plain information of the patient—e.g., patient's clear name, etc.—comprised in or associated with the medical data may be replaced with the at least one pseudonymized identifier to obtain pseudonymized medical data. Then, the pseudonymized medical data can be transmitted to, stored in, and retrieved from the long-term data repository.

According to various examples, the long-term data repository may comprise at least one of a cloud storage system, an edge storage system, or a combination of both outside the hospital. Such a cloud storage system may be public cloud storage, private cloud storage, or hybrid cloud storage.

According to various examples, the plain information of patients may be stored in the hospital local network, such as PACS, and the long-term data repository may retrieve corresponding plain information based on at least one pseudonymized identifier, such as a pseudonymized identity number, or at least one plain identifier, such as an identity number. In case of at least one pseudonymized identifier, the at least one computing device within the hospital local network may executing a reverse transformation associated with the function or the lookup table to derive plain information of the patient from the at least one pseudonymized identifier and then retrieve other plain information of the patient based on the derived plain information from the PACS. In case of at least one plain identifier, the at least one computing device within the hospital local network may retrieve other plain information of the patient based on the at least one plain identifier from the PACS.

According to the disclosure, to perform the longitudinal analysis of a pathology or disease of the patient, the medical data may be processed based on the prior medical result information. There are various options for considering the prior medical result information. For example, both the medical data and the prior medical result information may be fed to a machine-learning algorithm or another algorithm to determine current medical result information of the patient and thereby perform the longitudinal analysis of diseases of the patient. In a further example, only the medical data is fed to a machine-learning algorithm or another algorithm to determine the medical result information of the patient. Then, the medical result information may be compared with the prior medical result information, for performing the longitudinal analysis of diseases of the patient.

Generally, the prior medical result information and the current medical result information may be determined using the same or a different algorithm based on respective medical data obtained at a respective prior time point. In summary, the (current) medical result information and the prior medical result information may be determined using one and the same algorithm, e.g., a machine-learning algorithm, based on respective medical data.

FIG. 1 schematically illustrates details with respect to a system 1000 according to various examples. The system 1000 includes a long-term data repository 1001 outside a local network 1010 of a hospital or an institution.

For example, the long-term data repository 1001 may be located in an external network (not shown in FIG. 1), such as the Internet. The long-term data repository can thus be labeled as long-term cloud storage.

Also illustrated in FIG. 1 is a cloud server 1009. The cloud server 1009 can obtain medical data from the local network 1010. The cloud server 1009 can process the medical data, e.g., using a longitudinal analysis. The cloud server 1009 can also retrieve data from the long-term data repository 1001. For instance, the cloud server 1009 could retrieve medical result information from the long-term data repository 1001. For this purpose, the cloud server 1009 can determine at least one pseudonymized identifier based on which the medical result information is stored in the long-term data repository. The cloud server 1009 can also scrub patient clear information, in particular where it is associated with patient health information, by deleting any medical data that is linked to a unique patient identifier.

The local network 1010 may comprise at least one medical equipment 1002a-1002e, at least one local data repository 1003 comprising a PACS 1006, at least one computing device 1004 connectable to the long-term data repository 1001 via the external network/shared network, such as internet or a cloud. The computing device 1004 can act as gateway node to connect to the outside of the local network 1010, e.g., to the cloud server 1009. The local network 1010 further comprises at least one user terminal 1005a-1005c, which is generally optional. Within the local network 1010, each of the at least one medical equipment 1002a-1002e is respectively connectable to the at least one local data repository 1003 and the at least one computing device 1004 via physical cables or via wireless communication; each of the at least one user terminal 1005a-1005c may be connectable to the at least one computing device 1004 via physical cables or via wireless communication.

Generally, the cloud server 1009 is optional. In some scenarios, the computing device 1004 could directly access the long-term data repository 1001.

According to the disclosure, a workflow for processing medical data of a patient and thereby for performing a longitudinal analysis of diseases of the patient is provided. The workflow utilizes prior medical result information of the patient retrieved from a long-term data repository, such as 1001 of the system 1000, rather than original medical data, such as original medical imaging data; thereby, the workflow reduces the time for transferring the original medical data to or from the long-term data repository 1001, as well as storage spaces of the long-term data repository 1001. Details with respect to such workflow will be explained in connection with FIG. 2.

Figure 2:
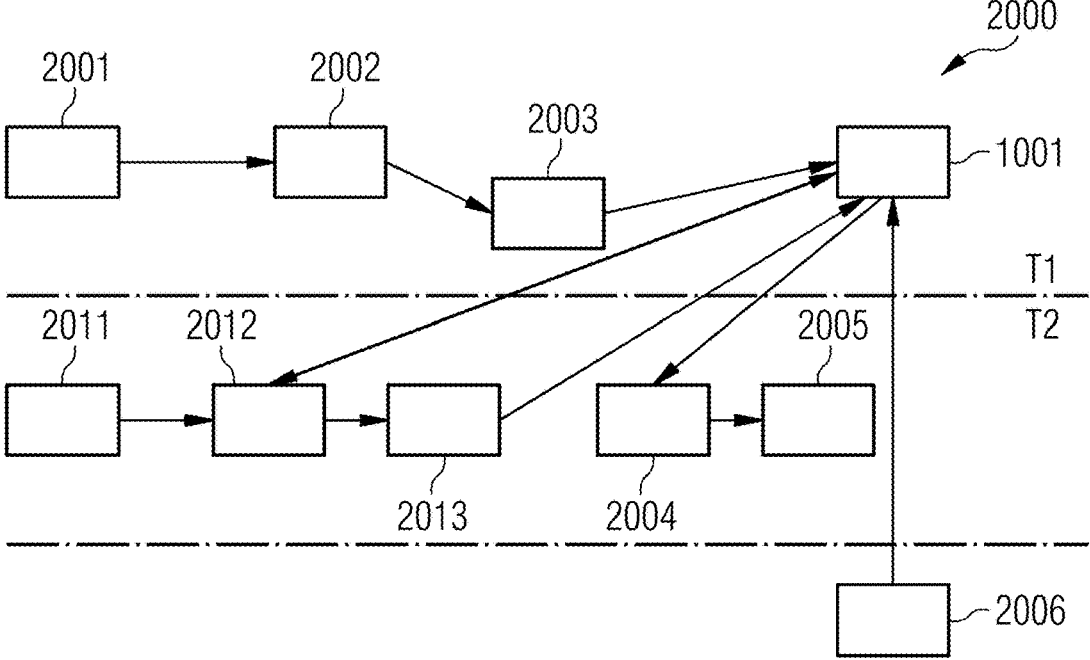
FIG. 2 schematically illustrates an exemplary workflow for processing medical data according to various examples.

FIG. 2 schematically illustrates an exemplary workflow 2000 for processing medical data according to various examples. The workflow 2000 pertains to processing the medical data, in particular performing a longitudinal analysis of diseases of the patient.

The workflow 2000 may be executed by a system comprising at least one computing device, or by the system 1000 of FIG. 1. Details of the workflow 2000 are described below.

Block 2001: at a first point in time T1, a first medical imaging examination is performed, by at least one of the medical equipment 1002a-1002e, with respect to an anatomical region of the patient. First medical imaging data is obtained by the first medical imaging examination and may be combined with plain information of the patient to construct first medical data, e.g., according to a standard, such as the DICOM standard. Other standards, such as JPEG or TIFF, may be used. The first medical data may be transmitted to the at least one local data repository 1003 and/or the at least one computing device 1004. The first medical data may be stored in the at least one local data repository 1003.

Generally, it is possible that medical imaging data and plain information of the patient is not framed into a common data structure, but rather retained as separate data structures, thus only logically defining the medical data.

Block 2002: the at least one computing device 1004 or the cloud server 1009, derives a first medical result information from the first medical imaging data, e.g., by executing an AI algorithm, such as a machine-learning algorithm.

Additionally or alternatively, the at least one computing device 1004 or the cloud server 1009 may determine at least one pseudonymized identifier associated with the patient based on the plain information of the patient. The first medical data may be pseudonymized by replacing the plain information with the at least one pseudonymized identifier to obtain first pseudonymized medical data, for example, by replacing data associated with the plain information within the header of a DICOM image file with those associated with the at least one pseudonymized identifier.

Additionally or alternatively, first medical result information may be also pseudonymized based on the at least one pseudonymized identifier to obtain first pseudonymized medical result information. For example, elements of the first medical result information may be encoded and stored in the part of a DICOM image file that is used to contain all pixel intensity data, and the at least one pseudonymized identifier is encoded and stored in the header part of the DICOM image file.

Block 2003: the first medical result information may be transmitted to and stored in the at least one local data repository 1003, such as the PACS 1006. Additionally or alternatively, the first pseudonymized medical data and/or the first pseudonymized medical result information may be transmitted to and stored in the long-term data repository 1001.

Additionally or alternatively, the first medical result information may be presented to a user (e.g. radiologist or the patient), via the at least one user terminal 1005a-1005c, for supporting an assessment of diseases of the patient.

Block 2011: similar to block 2001, at a second point in time T2 (T2 is later than T1, e.g., days or weeks later), a second medical imaging examination is performed, by at least one of the medical equipment 1002a-1002e, with respect to the anatomical region of the patient. Preferably, the second medical imaging examination is performed by the same type of medical equipment 1002a-1002e as that of the first medical imaging examination. Second medical imaging data is obtained by the second medical imaging examination and may be combined with the plain information of the patient to construct second medical data according to standards, such as the Digital Imaging and Communications in Medicine (DICOM) standard. The second medical data may be transmitted to the at least one local data repository 1003 and/or the at least one computing device 1004. The second medical data may be stored in the at least one local data repository 1003.

Block 2012: the at least one computing device 1004 or the cloud server 1009 may determine at least one pseudonymized identifier associated with the patient based on the plain information of the patient.

Additionally, the at least one computing device 1004 or the cloud server 1009 may transmit a query message to the long-term data repository 1001 for retrieving prior medical result information of the patient. The query message may be constructed based on the at least one pseudonymized identifier. I.e., the query message may not reveal plain information of the patient, e.g., may not reveal the patient's clear name, etc. The query message may include the at least one pseudonymized identifier. The query message may also include only a part of the pseudonymized identifier.

If there is prior medical result information of the patient stored in the long-term data repository 1001, such as the first pseudonymized medical result information, the long-term data repository 1001 will provide such prior medical result information in response to the query message.

Thereby, the at least one computing device 1004 or the cloud server 1009, by executing an AI algorithm, such as a machine-learning algorithm, derives second medical result information from the second medical imaging data; this is based on the prior medical result information. For instance, the second medical result information may be determined as a relative change with respect to the prior medical result information.

If there is no prior medical result information of the patient stored in the long-term data repository 1001, the at least one computing device 1004 or the cloud server 1009, by executing an AI algorithm, such as a machine-learning algorithm, derives a second medical result information from the second medical imaging data.

Additionally or alternatively, the second medical data may be pseudonymized by replacing the plain information with the at least one pseudonymized identifier to obtain second pseudonymized medical data, for example, by replacing data associated with the plain information within the header of a DICOM image file with those associated with the at least one pseudonymized identifier. Additionally or alternatively, like pseudonymizing the second medical data, the second medical result information may be also pseudonymized based on the at least one pseudonymized identifier to obtain second pseudonymized medical result information. For example, elements of the second medical result information may be encoded and stored in the part of a DICOM image file that is used to contain all pixel intensity data, and the at least one pseudonymized identifier is encoded and stored in the header part of the DICOM image file.

Block 2013: the second medical result information may be transmitted to and stored in the at least one local data repository 1003, such as the PACS 1006. Additionally or alternatively, the second pseudonymized medical data and/or the second pseudonymized medical result information may be transmitted to and stored in the long-term data repository 1001.

Additionally or alternatively, the second medical result information may be presented to a user (e.g. radiologist or the patient), via the at least one user terminal 1005a-1005c, for supporting an assessment of diseases of the patient. For instance, the second medical result information may be presented along with the prior medical result information. Thereby, a relative change may be judged by the user. A longitudinal analysis becomes possible.

The same blocks 2011-2013 may be performed based on a third medical data comprising a third medical imaging data obtained during a third medical examination at a third point in time T3 (T3 is later than T2). The only difference is that the at least one computing device 1004 or the cloud server 1009 may derive, by executing an AI algorithm, such as a machine-learning algorithm, a third medical result information from the third medical imaging data and based on the second medical result information only or on both the first and second medical result information together. I.e., the current medical result information may be determined based on at least one prior medical result information.

Optionally or additionally, the workflow 2000 may further comprise:

Block 2004: the at least one computing device 1004 or the cloud server 1009 may retrieve at least two prior medical result information from the long-term data repository 1001 based on the at least one pseudonymized identifier associated with the patient. I.e., a multi-time-point longitudinal analysis is possible.

Block 2005: the at least one computing device 1004 or the cloud server 1009 may compare the at least two prior medical result information to perform a longitudinal analysis of diseases.

Block 2006: the at least one computing device 1004 or the cloud server 1009 may send a deletion message to the long-term data repository 1001 for deleting at least one of specific prior medical result information of a patient, all prior medical result information of the patient, all prior medical result information determined within a time duration, all the medical result information transmitted from a specific hospital, and etc. The deletion message may be constructed based on the at least one pseudonymized identifier. For example, the deletion message may comprise a pseudonymized identity number and pseudonymized date of determination of the specific prior medical result information. Other message structures in the prior art may also be adopted herein.

Alternatively or additionally, it would also be possible to scrub all clear patient information at the cloud server 1009. I.e., it would be possible to delete medical data, at least if stored in connection with a non-pseudonymized patient identifier or, generally, clear patient information. For instance, images associated with a unique patient ID or patient clear name, may be deleted at the cloud server 1009. Thereby, data retention may be limited to a certain time required for the performing of the longitudinal analysis.

According to various examples, when taking into account certain medical result information from a previous time point, it may be preferable to ensure that this previous medical result information in fact relates to the same patient as currently under examination. Since the medical result information from previous time points may be stored in a pseudonymized way, additional checks may be performed. This helps to resolve ambiguities between different pseudonymized identifiers. For instance, where clear information such as patient name is subject to data minimization, the pseudonymized identifiers are not guaranteed to be unique—even within on hospital institution.

According to the disclosure, retrieving prior medical result information of the patient from the long-term data repository 1001 based on the at least one pseudonymized identifier may comprise: the at least one computing device 1004 or the cloud server 1009 may retrieve the prior medical result information of the patient based on the at least one pseudonymized identifier from the long-term data repository 1001; the at least one computing device 1004 or the cloud server 1009 may parse the prior medical result information to obtain further plain information (further first information) of the patient or a further patient, and thereby determine whether the prior medical result information belongs to the patient based on a comparison between the plain information and the further plain information. In detail, the prior medical result information may include or be associated with a further at least one pseudonymized identifier. This further at least one pseudonymized identifier may be translated into the further plain information, e.g., based on a mapping or look-up table. Such process can be referred to as patient matching. Patient matching can be executed as part of block 2012. Patient matching can be executed by the at least one computing device 1004 or the cloud server 1009. Details with respect to patient matching will be described in FIG. 3.

Figure 3:
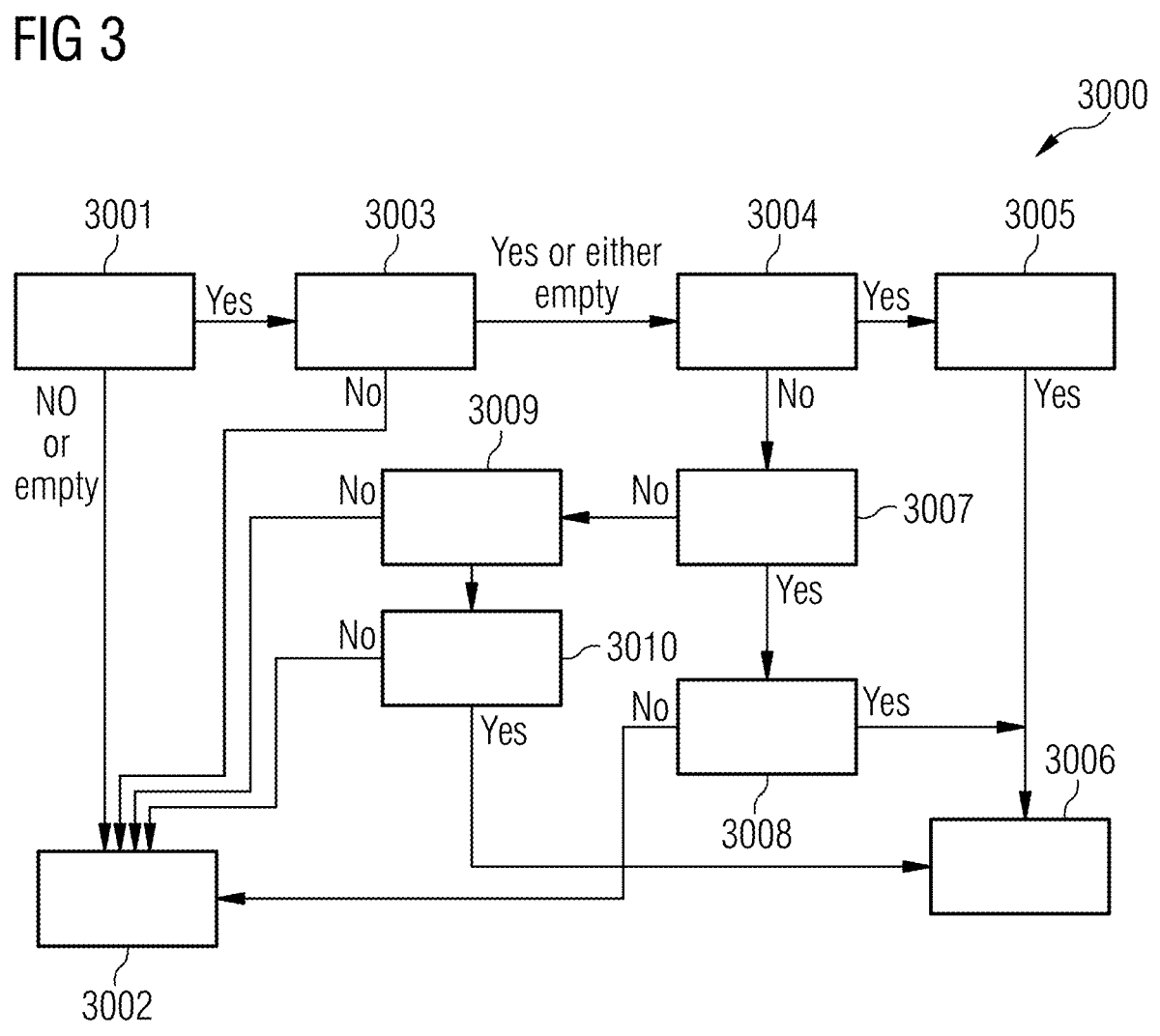

FIG. 3 schematically illustrates an exemplary method 3000 for patient matching according to various examples.

The method 3000 may be executed by a computer comprising at least one processing unit, or by the at least one computing device 1004 of the system 1000 of FIG. 1. The method may, at least in parts, be executed by the cloud server 1009.

The method 3000 pertains to determining whether the prior medical result information belongs to a given patient or not, in particular determining whether the prior medical result information belongs to the given patient. This is based on a comparison between multiple information elements associated with either plain information the patient associated with medical data and further plain information; or with at least one pseudonymized identifier associated with the medical data and at least one further pseudonymized identifier associated with or even included in the prior medical result information.

In some examples, the further plain information of the patient can be obtained from the at least one further pseudonymized identifier associated with or included in the prior medical result information (i.e., by parsing the prior medical result information). This means that the pseudonymized patient identifier is mapped to plain information of the patient that serves as a comparison target against the current plain information. Depending on whether a one-to-one or one-to-many mapping is used, such parsing may yield ambiguities. Such ambiguities may be resolved by comparing multiple information elements, as illustrated below in connection with FIG. 3.

Details of the method 3000 are described below. The method is explained, for sake of simplicity, for clear representations of the respective information elements, but could be likewise implemented for pseudonymized representations of the respective information elements.

Block 3001: a comparison between the respective patient ID of the plain information and of the further plain information is performed.

If the patient ID of the plain information is empty, which may indicate there is no prior medical result information of the patient available, or if the respective patient ID of the plain information and the further plain information are not the same, then, at block 3002, it is possible to determine that the prior medical result information does not belong to the patient.

If the respective patient ID of the plain information and the further plain information are the same, at block 3003, it is possible to check the respective issuer of patient ID of the plain information and of the further plain information.

If the respective issuer of patient ID of the plain information and the further plain information are not the same, block 3002, it is possible to determine that the prior medical result information does not belong to the patient.

If the issuer of patient ID of the plain information is empty, or if the issuer of patient ID of the plain information and the further plain information are the same, at block 3004, it is possible to check whether patient name, date of birth, and gender are all present in the plain information.

If the patient name, the date of birth, and the gender are all present in the plain information and, at block 3005, at least two of them are the same as those of the further plain information, at block 3006, it is possible to determine that the prior medical result information does belong to the patient.

If, at block 3007, at least two of the patient name, date of birth, and gender are present in the plain information, and if, at block 3008, at least one of the respective patient name, date of birth, and gender of the plain information and of the further plain information is the same, at block 3006, it is possible to determine that the prior medical result information belongs to the patient.

If, at block 3009, only one of the patient name, date of birth, and gender is present in the plain information, and if, at block 3010, the only one of the respective patient name, date of birth, and gender of the plain information and of the further plain information is the same, at block 3006, it is possible to determine that the prior medical result information belongs to the patient.

Otherwise, at block 3002, it is possible to determine that the prior medical result information does not belong to the patient.

The patient matching explained above is only one example. Various implementations of the patient matching are conceivable. Generally, where the plain information and the further plain information each include multiple corresponding information elements, a comparison can be implemented in accordance with a predefined hierarchical ruleset that defines a sequence of sub-comparisons (specified by the blocks 3004, 3005, etc.) between at least two of the corresponding information elements.

Further, the comparison is illustrated in FIG. 3 is implemented based on plain information. According to various examples, it would also be possible that pseudonymized patient information and the respective information elements as outlined above are available in the respective pseudonymized representations, e.g., hash values, etc. Then, respective comparisons may also be implemented based on the pseudonymized representations of the information elements of the pseudonymized identifier associated with the patient.

Also, mixed scenarios are conceivable where some information elements are available in a clear representation and others are available in a pseudonymized representation.

Figure 4:
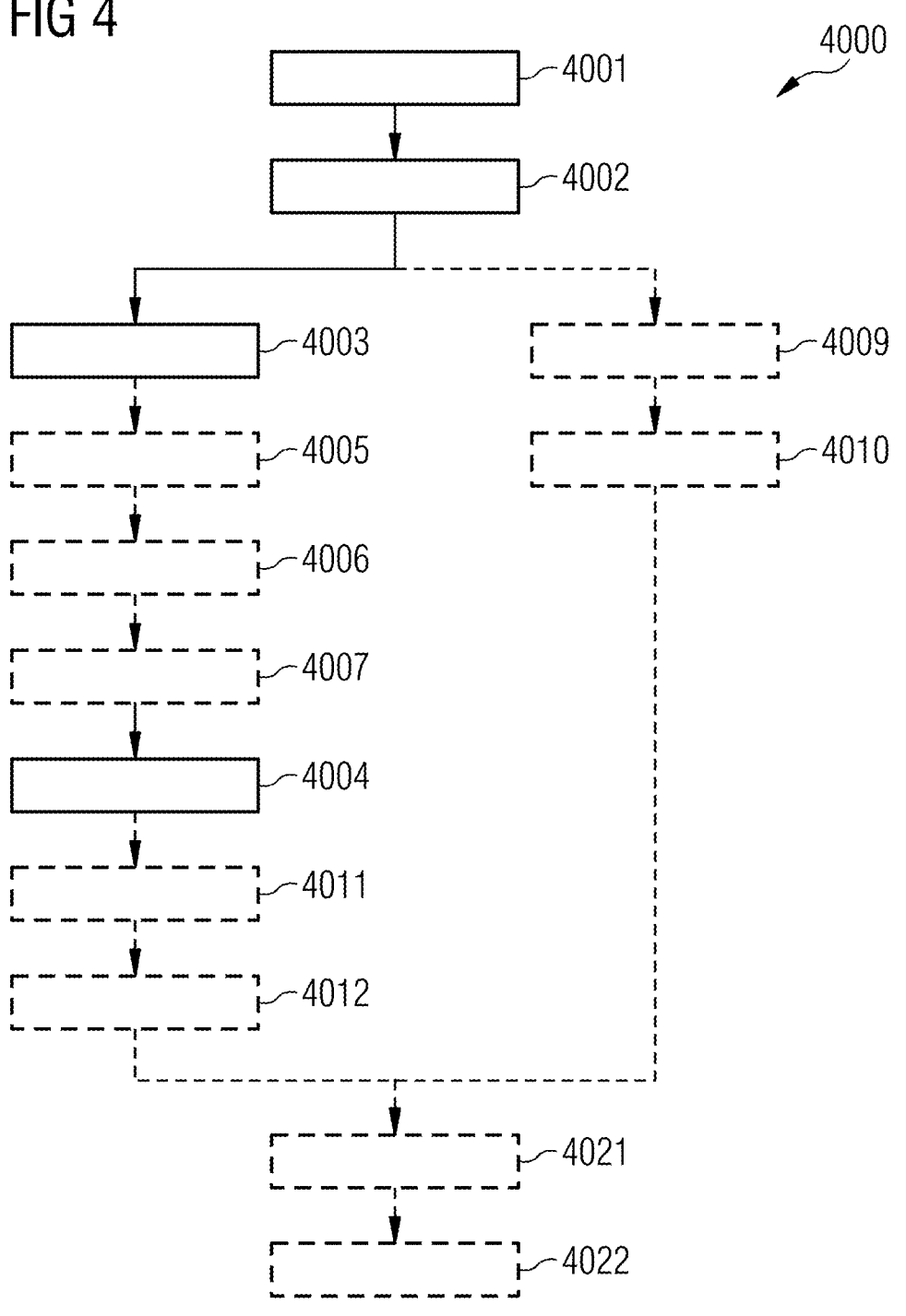
FIG. 4 is a flowchart of a method according to various examples.

FIG. 4 is a flowchart of a method 4000 for processing medical data of a patient. The method 4000 pertains to processing medical data of a patient, in particular performing a longitudinal analysis of diseases of the patient. The method 4000 can facilitate the workflow of FIG. 2 by implementing at least parts of the workflow.

Optional blocks are labeled with dashed lines.

The method may be executed by a computer comprising at least one processing unit, specifically by the at least one computing device 1004 within the hospital local network 1010 and connectable to an external network, the external network comprising the long-term data repository 1001. The method of FIG. 4 may be executed, at least in parts, by the cloud server. It would be possible that parts of the method are executed by the cloud server 1009 and other parts are executed by the computing device 1004. For instance blocks 4001 and 4002 may be executed by the computing device 1004, while the remaining blocks may be executed by the cloud server 1009. Details of the method 4000 are described below.

Block 4001: medical data comprising medical imaging data captured for an anatomical region of the patient and plain information of the patient is obtained. The medical data may be obtained from at least one medical equipment 1002a-1002e or from the at least one local data repository 1003, such as the PACS 1006.

The medical data may be obtained in a push communication at the cloud server 1009, the push communication being initiated by the computing device 1004. Accordingly, the computing device 1004 may act as a gateway node facilitating the cloud connectivity.

Block 4002: at least one pseudonymized identifier associated with the patient is determined based on the plain information of the patient. The at least one pseudonymized identifier may be determined by using techniques outlined above.

Block 4003: prior medical result information of the patient is retrieved from a long-term data repository 1001 based on the at least one pseudonymized identifier. Here, the prior medical result information may be the first and/or the second pseudonymized medical result information described above.

Optionally, retrieving the prior medical result information may comprise transmitting a query message to the long-term data repository 1001, the query message being constructed based on the at least one pseudonymized identifier.

Block 4004: the medical data is processed based on the at least one prior medical result information. For example, both the medical data and the at least one prior medical result information may be fed to an algorithm, such as a machine-learning algorithm. Alternatively, only the medical data is fed to an algorithm, and medical result information is obtained. Then, the medical result information can be compared with the prior medical result information. This corresponds to a longitudinal analysis. It is thus possible to determine the medical result information based on the medical data.

For instance, such algorithm could quantify a size or a pathology state of a tumor. The algorithm could extract quantitative or qualitative medical indicators from medical imaging data. Respective algorithms are per se known and the particular implementation is not germane for the functioning of the techniques disclosed herein.

Then, the medical result information and the at least one prior medical result information may be compared by using a further algorithm. This can include determining a quantitative or qualitative change, e.g., a shape change of a region-of-interest, a size increase or decrease, etc.

For illustration, it would be possible that the medical data is processed by the computing device 1004, i.e., within the local network 1010. In such a scenario, the medical data may be retained in the local network 1010 and a respective query message being constructed based on the at least one pseudonymized identifier may be provided to the cloud server 1009 and onwards to the long-term data repository 1001. In this scenario, plain information of the patient and medical data may be retained within the local network 1010 and not exposed to a shared network. The pseudonymized identifier may be determined at the computing device 1004 within the local network 1010, at block 4002.

In another scenario, it would be possible that the pseudonymized identifier is determined at the cloud server 1009. Then, at least for some time, the plain information of the patient may be buffered at the cloud server 1009, outside of the hospital local network 1010. In such a scenario, it would be possible that the medical data is processed at the cloud server 1009. The cloud server 1009 can perform the longitudinal analysis and provide a result to the computing device 1004 within the hospital local network 1010. It would also be possible that the medical data is processed at the computing device 1004; in such a scenario, the computing device 1004 may retain the medical data locally, i.e., not pass the medical data onwards to the cloud server 1009 and subsequently receive the prior medical result information from the cloud server 1009. Here, only the plain information of the patient is exposed to the shared network, however, without associated medical data. Then, the computing device 1004 can perform the longitudinal analysis.

As will be appreciated from the above, various distributions of logic between the computing device 1004 and the cloud server 1009 are conceivable, depending on a degree of exposure of patient information and medical data to the outside of the hospital local network 1010.

Optionally, the method 4000 may further comprise:

Block 4005: further plain information of the patient or a further patient may be optionally obtained by parsing the prior medical result information. Parsing may correspond to transcribing a further pseudonymized patient identifier of the prior medical result information into clear information elements, i.e., plain information. Said parsing may be executed by using the reverse transformation associated with the function or the lookup table described above.

Block 4006: it is optionally possible to determine whether the prior medical result information belongs to the patient based on a comparison between the plain information and the further plain information, or—if no parsing is executed—based on a comparison of the pseudonymized identifier and the further pseudonymized patient identifier of the prior medical result information. This corresponds to patient matching.

Said determining may be performed by using the method 3000 outlined above.

According to the disclosure, the plain information and the further plain information each may include multiple corresponding information elements as outlined above, and the comparison is implemented in accordance with a predefined hierarchical ruleset defining a sequence of sub-comparisons between at least two of the corresponding information elements.

It would also be possible that the pseudonymized patient identifier and the further pseudonymized patient identifier each may include multiple corresponding information elements as outlined above, and the comparison is implemented in accordance with a predefined hierarchical ruleset defining a sequence of sub-comparisons between at least two of the corresponding information elements.

If the prior medical result information belongs to the patient, then block 4004 is executed. If not, executing the method 4000 is stopped or only the medical data is processed to obtain medical result information as described above in connection with FIG. 2.

Optionally, the method may further comprise:

Block 4009: it is possible to replace the plain information comprised in the medical data with the at least one pseudonymized identifier to obtain pseudonymized medical data.

Block 4010: the pseudonymized medical data can be transmitted to the long-term data repository to be stored therein.

Optionally, the method 4000 may further comprise:

Block 4007: It would be optionally possible to query, at the local data repository 1003, auxiliary data to facilitate the longitudinal analysis at box 4004. For instance, the auxiliary data can pertain to further medical data. The auxiliary data could pertain to medical context information, e.g., when imaging modality of the at least one medical equipment 1002a-1002e. The auxiliary data can be patient specific.

For instance, such a query could be triggered based on a lookup table which links plain information of the patient and/or pseudonymized identifiers to respective entries of the local data repository 1003. For instance, it would be possible that the cloud server 1009 determines, based on the at least one pseudonymized identifier, that a respective entry including auxiliary data is available in the local data repository 1003. Then, the cloud server 1009 can provide a respective query to the computing device 1004 which may then retrieve the auxiliary data and provide the auxiliary data to the cloud server 1009. The medical data may be processed based on the prior medical result information as well as the auxiliary data. The longitudinal analysis may be implemented taking into account the auxiliary data.

In another example, where the longitudinal analysis is implemented by the computing device 1004, it would be possible that the cloud server 1009 provides a respective pointer to the auxiliary data to the computing device 1004 and the computing device 1004 may then retrieve the auxiliary data from the local data repository 1003 to perform the longitudinal analysis. The computing device 1004 may process the medical data based on the prior medical result information provided by the cloud server 1009 as well as based on the auxiliary data.

Block 4011: it is possible to pseudonymize the medical result information based on the at least one pseudonymized identifier.

Block 4012: the pseudonymized medical result information can be transmitted to the long-term data repository to be stored therein.

Optionally, the method may further comprise:

Block 4021: receiving a message from the long-term data repository, the message indicating that storage space of the long-term data repository is approaching capacity. The, the at least one computing device 1004 may send a deletion message to the long-term data repository.

Block 4022: if patient information is retained in a clear representation (i.e., not a pseudonymized representation) outside the local hospital network 1010 at the cloud server 1009, it would be possible to delete/scrub such information. For instance, plain information of the patient stored at the cloud server 1009 to determine the pseudonymized identifier may be deleted. It would be possible to delete medical data stored at the cloud server 1009. Only medical result information may be retained at the long-term data repository 1001.

Figure 5:
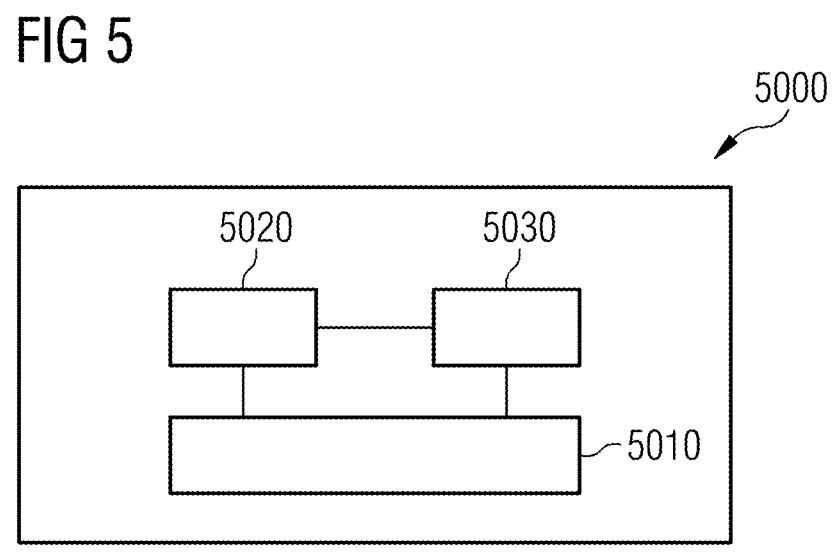

FIG. 5 is a block diagram of a device 5000 according to various examples. The device 5000 can be configured to process medical data of a patient, in particular performing a longitudinal analysis of diseases of the patient, by executing the method 4000 outlined above. For example, the device 5000 may implement the at least one computing device 1004 of FIG. 1. It would be possible that the device 5000 implements the cloud server 1009 of FIG. 1. The device 5000 could also be part of a medical equipment 1002a-1002e (cf. FIG. 1).

The device 5000 may comprise at least one computing unit 5020, at least one memory 5030, and at least one input/output interface 5010. The at least one computing unit 5020 is configured to load program code from the at least one memory 5030 and execute the program code. Upon executing the program code, the at least one computing unit 5020 performs the method 4000 of processing medical data of a patient.

Summarizing, techniques have been described that facilitate retrieving prior medical result information and/or medical data of a specific patient from a long-term data repository outside a local hospital network while data privacy can be ensured. At least one pseudonymized identifier associated with the patient may be used to identify the prior medical result information and/or the medical data and the retrieving is performed based on the at least one pseudonymized identifier. Meanwhile, storage burdens on local hospital storage, such as the PACS, can be significantly relieved by just temporarily storing medical data and/or medical result information of patients in the local hospital storage. Additionally, if only medical result information of patients is stored in the long-term data repository, time for transferring data of patients to or from the long-term data repository is reduced and storage spaces for storing the data of patients also reduced.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the disclosure has been shown and described with respect to certain preferred embodiments, equivalents and modifications will occur to others skilled in the art upon the reading and understanding of the specification. The present disclosure includes all such equivalents and modifications and is limited only by the scope of the appended claims.

The invention claimed is:

1. A computer-implemented method, the method comprising:

processing, by processing circuitry, first medical data to generate prior medical result information;

sending, by the processing circuitry, the prior medical result information to a long-term data repository without sending the first medical data to the long-term data repository;

obtaining, by the processing circuitry, second medical data comprising medical imaging data and non-pseudonymized information of a patient, the medical imaging data captured for an anatomical region of the patient;

generating, by the processing circuitry, at least one pseudonymized identifier associated with the patient, the generating being performed based on the non-pseudonymized information of the patient;

transmitting, by the processing circuitry, a query message to the long-term data repository for retrieving the prior medical result information from the long-term data repository, the query message being constructed based on the at least one pseudonymized identifier;

processing, by the processing circuitry, the second medical data based on the prior medical result information; and causing, by the processing circuitry, the long-term data repository to delete the prior medical result information by sending a deletion message to the long-term data repository, the deletion message including the at least one pseudonymized identifier.

2. The computer-implemented method of claim 1, wherein a shared network includes the long-term data repository; and at least one computing device includes the processing circuitry, the at least one computing device being within a hospital local network and connectable to the shared network.

3. The computer-implemented method of claim 2, wherein the generating generates the at least one pseudonymized identifier based on a salted secure hash function, the at least one pseudonymized identifier including a salted hash value, and a salt of the salted hash value corresponding to the hospital local network.

4. The computer-implemented method of claim 1, wherein the generating generates the at least one pseudonymized identifier based on the non-pseudonymized information using a function or a lookup table.

5. The computer-implemented method of claim 4, further comprising:

parsing the prior medical result information to obtain further non-pseudonymized information of the patient or of a further patient; and determining whether the prior medical result information is associated with the patient based on a comparison between the non-pseudonymized information and the further non-pseudonymized information.

6. The computer-implemented method of claim 5, wherein the non-pseudonymized information and the further non-pseudonymized information each include multiple corresponding information elements; and the comparison is implemented in accordance with a hierarchical ruleset defining a sequence of sub-comparisons between at least two of the multiple corresponding information elements.

7. The computer-implemented method of claim 4, further comprising:

obtaining at least one further pseudonymized identifier associated with the prior medical result information; and determining whether the prior medical result information is associated with the patient based on a comparison between the at least one pseudonymized identifier and the at least one further pseudonymized identifier.

8. The computer-implemented method of claim 7, wherein the at least one pseudonymized identifier and the at least one further pseudonymized identifier each include multiple corresponding information elements; and the comparison is implemented in accordance with a hierarchical ruleset defining a sequence of sub-comparisons between at least two of the multiple corresponding information elements.

9. The computer-implemented method of claim 1, further comprising:

parsing the prior medical result information to obtain further non-pseudonymized information of the patient or of a further patient; and determining whether the prior medical result information is associated with the patient based on a comparison between the non-pseudonymized information and the further non-pseudonymized information.

10. The computer-implemented method of claim 9, wherein the non-pseudonymized information and the further non-pseudonymized information each include multiple corresponding information elements; and the comparison is implemented in accordance with a hierarchical ruleset defining a sequence of sub-comparisons between at least two of the multiple corresponding information elements.

11. The computer-implemented method of claim 1, further comprising:

obtaining at least one further pseudonymized identifier associated with the prior medical result information; and determining whether the prior medical result information is associated with the patient based on a comparison between the at least one pseudonymized identifier and the at least one further pseudonymized identifier.

12. The computer-implemented method of claim 11, wherein the at least one pseudonymized identifier and the at least one further pseudonymized identifier each include multiple corresponding information elements; and the comparison is implemented in accordance with a hierarchical ruleset defining a sequence of sub-comparisons between at least two of the multiple corresponding information elements.

13. The computer-implemented method of claim 1, further comprising:

determining first medical result information based on the second medical data; and comparing the prior medical result information and the first medical result information to perform a longitudinal analysis.

14. The computer-implemented method of claim 1, further comprising:

replacing the non-pseudonymized information with the at least one pseudonymized identifier to obtain pseudonymized medical data; and transmitting the pseudonymized medical data to the long-term data repository.

15. The computer-implemented method of claim 1, further comprising:

determining first medical result information based on the second medical data;

pseudonymizing the first medical result information based on the at least one pseudonymized identifier to obtain pseudonymized medical result information; and transmitting the pseudonymized medical result information to the long-term data repository.

16. The computer-implemented method of claim 1, wherein the processing processes the second medical data using a machine-learning algorithm to perform a longitudinal analysis of a pathology of the patient.

17. The computer-implemented method of claim 1, wherein the obtaining the second medical data comprises:

loading the second medical data from a picture archiving and communication system (PACS) within a hospital local network.

18. The computer-implemented method of claim 1, further comprising:

retrieving auxiliary data from a local repository based on the at least one pseudonymized identifier, the local repository being within a hospital local network, wherein the processing processes the second medical data based on the auxiliary data.

19. The computer-implemented method of claim 1, wherein the non-pseudonymized information includes at least one of an identity number, an issuer of the identity number, a name, a date of birth, a gender, or an original unique identity number.

20. The computer-implemented method of claim 1, further comprising:

obtaining the medical imaging data from a medical imaging scanner during a medical imaging examination of the anatomical region of the patient, the medical imaging scanner being a magnetic resonance imaging (MRI) scanner, a computed tomography (CT) scanner, an X-ray scanner, a positron emission tomography (PET) scanner, a single-photon emission computed tomography (SCPET) scanner, a hematology analyzer, an electroencephalogram (EEG) or an electrocardiogram;

constructing the second medical data based on the medical imaging data; and presenting a result of the processing of the second medical data via a user terminal.

21. The computer-implemented method of claim 1, further comprising:

generating pseudonymized medical data by incorporating the at least one pseudonymized identifier into a header of the second medical data, wherein the processing includes processing the pseudonymized medical data based on the prior medical result information.

22. The computer-implemented method of claim 1, wherein the medical imaging data of the second medical data is captured by a first type of medical imaging scanner;

the processing includes processing the second medical data using a first algorithm to obtain first medical result information;

the method further comprises comparing, by the processing circuitry, the prior medical result information and the first medical result information to perform a longitudinal analysis; and one of:

the processing the first medical data includes processing the first medical data using the first algorithm, or the first medical data is captured by the first type of medical imaging scanner.

23. A device comprising:

processing circuitry configured to cause the device to, process first medical data to generate first medical result information, send the first medical result information to a long-term data repository without sending the first medical data to the long-term data repository, obtain second medical data comprising medical imaging data and non-pseudonymized information of a patient, the medical imaging data captured for an anatomical region of the patient, generate at least one pseudonymized identifier associated with the patient, the generation being performed based on the non-pseudonymized information of the patient, transmit a query message to the long-term data repository for retrieving the first medical result information from the long-term data repository, the query message being constructed based on the at least one pseudonymized identifier, process the second medical data based on the first medical result information, and cause the long-term data repository to delete the first medical result information by sending a deletion message to the long-term data repository, the deletion message including the at least one pseudonymized identifier.

24. A non-transitory computer readable medium comprising instructions that, when executed by processing circuitry of a computing device, cause the computing device to:

process first medical data to generate first medical result information, send the first medical result information to a long-term data repository without sending the first medical data to the long-term data repository, obtain second medical data comprising medical imaging data and non-pseudonymized information of a patient, the medical imaging data captured for an anatomical region of the patient, generate at least one pseudonymized identifier associated with the patient, the generation being performed based on the non-pseudonymized information of the patient, transmit a query message to the long-term data repository for retrieving the first medical result information from the long-term data repository, the query message being constructed based on the at least one pseudonymized identifier, process the second medical data based on the first medical result information, and cause the long-term data repository to delete the first medical result information by sending a deletion message to the long-term data repository, the deletion message including the at least one pseudonymized identifier.

* * * * *